US012559478B2

(12) United States Patent
Hamilton

(10) Patent No.: US 12,559,478 B2
(45) Date of Patent: Feb. 24, 2026

(54) CO-CRYSTAL FORMS OF SELINEXOR

(71) Applicant: Karyopharm Therapeutics Inc., Newton, MA (US)

(72) Inventor: Clifton Hamilton, Devens, MA (US)

(73) Assignee: Karyopharm Therapeutics Inc., Newton, MA (US)

(*) Notice: Subject to any disclaimer, the term of this patent is extended or adjusted under 35 U.S.C. 154(b) by 1022 days.

(21) Appl. No.: 17/446,664

(22) Filed: Sep. 1, 2021

(65) Prior Publication Data

US 2021/0395232 A1 Dec. 23, 2021

Related U.S. Application Data

(63) Continuation of application No. PCT/US2020/023530, filed on Mar. 19, 2020.

(60) Provisional application No. 62/821,203, filed on Mar. 20, 2019.

(51) Int. Cl.

| | |
|---|---|
| ***C07D 403/12*** | (2006.01) |
| ***C07C 47/58*** | (2006.01) |
| ***C07C 55/10*** | (2006.01) |

(52) U.S. Cl.

CPC ............ *C07D 403/12* (2013.01); *C07C 47/58* (2013.01); *C07C 55/10* (2013.01); *C07B 2200/13* (2013.01)

(58) Field of Classification Search

CPC .................................................... C07D 403/12

See application file for complete search history.

(56) References Cited

U.S. PATENT DOCUMENTS

| | | |
|---|---|---|
| 2018/0000808 A1 | 1/2018 | Stahly et al. |
| 2018/0230140 A1 | 8/2018 | Viertelhaus et al. |

FOREIGN PATENT DOCUMENTS

| | | | |
|---|---|---|---|
| CN | 107089946 A | 8/2017 |
| WO | WO-2011/067571 A1 | 6/2011 |
| WO | WO-2013/019548 A1 | 2/2013 |
| WO | WO-2016/025904 A1 | 2/2016 |
| WO | WO-2017/118940 A1 | 7/2017 |
| WO | WO-2018/129227 A1 | 7/2018 |
| WO | WO-2020/191140 A1 | 9/2020 |

OTHER PUBLICATIONS

International Search Report and Written Opinion for International Application No. PCT/US20/23530 dated Jun. 5, 2020.

Karimi-Jafari et al., "Creating cocrystals: A review of pharmaceutical cocrystal preparation routes and applications." Crystal Growth & Design 18 (2018): 6370-6387.

Vishweshwar et al., "Pharmaceutical co-crystals." Journal of Pharmaceutical Sciences 95.3 (2006): 499-516.

"Assessment for applying cocrystals to pharmaceutical APIs and production of cocrystals", Pharmacia, 2013, vol. 49, No. 12, p. 1201.

Noriyuki, "Cocrystal screening and its application in improvement of physicochemical properties of APIs", Pharm Tech Japan, 2009, vol. 25, No. 12, p. 155-166.

Takata, "API form screening and selection in drug discovery stage", Pharm Stage, vol. 6, No. 10, Jan. 15, 2007, p. 20-25.

*Primary Examiner* — John S Kenyon

(74) *Attorney, Agent, or Firm* — FOLEY HOAG LLP

(57) ABSTRACT

The present invention is directed to selinexor co-crystal forms; more particularly to two co-crystal forms with succinic acid as the coformer and a co-crystal form with vanillin as the coformer. The present disclosure is also related to processes for the preparation of selinexor co-crystal forms. Further, the present invention also relates to pharmaceutical compositions comprising a selinexor co-crystal form and method for treating disease using a selinexor co-crystal form.

19 Claims, 16 Drawing Sheets

CO-CRYSTAL FORMS OF SELINEXOR

CROSS-REFERENCE TO RELATED APPLICATIONS

This application is a continuation of International Application No. PCT/US2020/023530, filed Mar. 19, 2020, which claims priority to U.S. Provisional Patent Application No. 62/821,203, filed Mar. 20, 2019, the disclosures of which are incorporated herein by reference in their entireties for all purposes.

FIELD OF THE DISCLOSURE

The present invention is directed to co-crystal forms of selinexor; particularly with succinic acid or vanillin as the co-crystal former (coformer). Further, the present disclosure is also related to processes for the preparation of the forms of selinexor co-crystals with succinic acid and the form of selinexor co-crystals with vanillin. Further, the present disclosure also relates to pharmaceutical compositions comprising these forms and to methods for treating disease using the forms.

BACKGROUND OF THE DISCLOSURE

Selinexor is orally available, small molecule inhibitor of CRM1 (chromosome region maintenance 1 protein, referred to as exportin 1 or XPO1) that is overexpressed in a variety of cancer cell types, and thus is useful for treating disorders associated with CRM1 such as cancer. Selinexor irreversibly inactivates CRM1-mediated nuclear export of cargo proteins such as tumor suppressor proteins (TSPs), including p53, p21, BRCA1/2, pRB, FOXO, and other growth regulatory proteins. Thus, selinexor's activity in being a selective inhibition of nuclear export (SINE), restores endogenous tumor suppressing processes to selectively eliminate tumor cells while sparing normal cells. Selinexor has the chemical designation (Z)-3-(3-(3,5-bis(trifluoromethyl)phenyl)-IH-I, 2,4-triazol-1-yl)-N'-(pyrazin-2yl)acrylohydrazide, and the following structure:

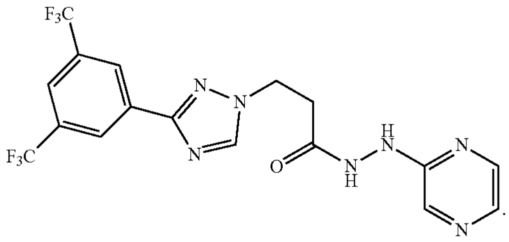 [SMILES: O=C(CCn1cnc(-c2cc(C(F)(F)F)cc(C(F)(F)F)c2)n1)NNc1cnccn1]

Selinexor is marketed under the trade name XPOVIO®. XPOVIO® is indicated in combination with dexamethasone for the treatment of adult patients with relapsed or refractory multiple myeloma (RRMM) who have received at least four prior therapies and whose disease is refractory to at least two proteasome inhibitors, at least two immunomodulatory agents, and an anti-CD38 monoclonal antibody.

Selinexor is also expected to be useful in treating acute myeloid leukemia, multiple myeloma, endometrial cancer, sarcoma, liposarcoma, glioma, diffuse large B-cell lymphoma, brain cancer, cervical cancer, ovarian cancer, head and neck cancer, foot ulcers, acute lymphocytic leukemia, colorectal cancer and Richter's transformation (SIRRT).

Selinexor is described in U.S. Pat. Nos. 8,999,996 and 9,714,226. Solid forms of selinexor are described in U.S. Pat. No. 10,519,139 (four patterns A-D) and U.S. Patent Publication Nos. 2019/0023693 (amorphous and fourteen patterns α-ξ), and 2019/0336499 (seventeen patterns T1-T17). None of the references describe any patterns resulting from a reaction wherein succinic acid or vanillin were present. Furthermore, none of the references disclose a co-crystal of selinexor; more particularly a co-crystal of selinexor with succinic acid or vanillin.

SUMMARY OF THE DISCLOSURE

The present invention is directed to selinexor co-crystal forms; more particularly to two co-crystal forms with succinic acid as the coformer and a co-crystal form with vanillin as the coformer. The present disclosure is also related to processes for the preparation of selinexor co-crystal forms. Further, the present invention also relates to pharmaceutical compositions comprising a selinexor co-crystal form and method for treating disease using a selinexor co-crystal form.

DETAILED DESCRIPTION OF THE DISCLOSURE

Figure 1:
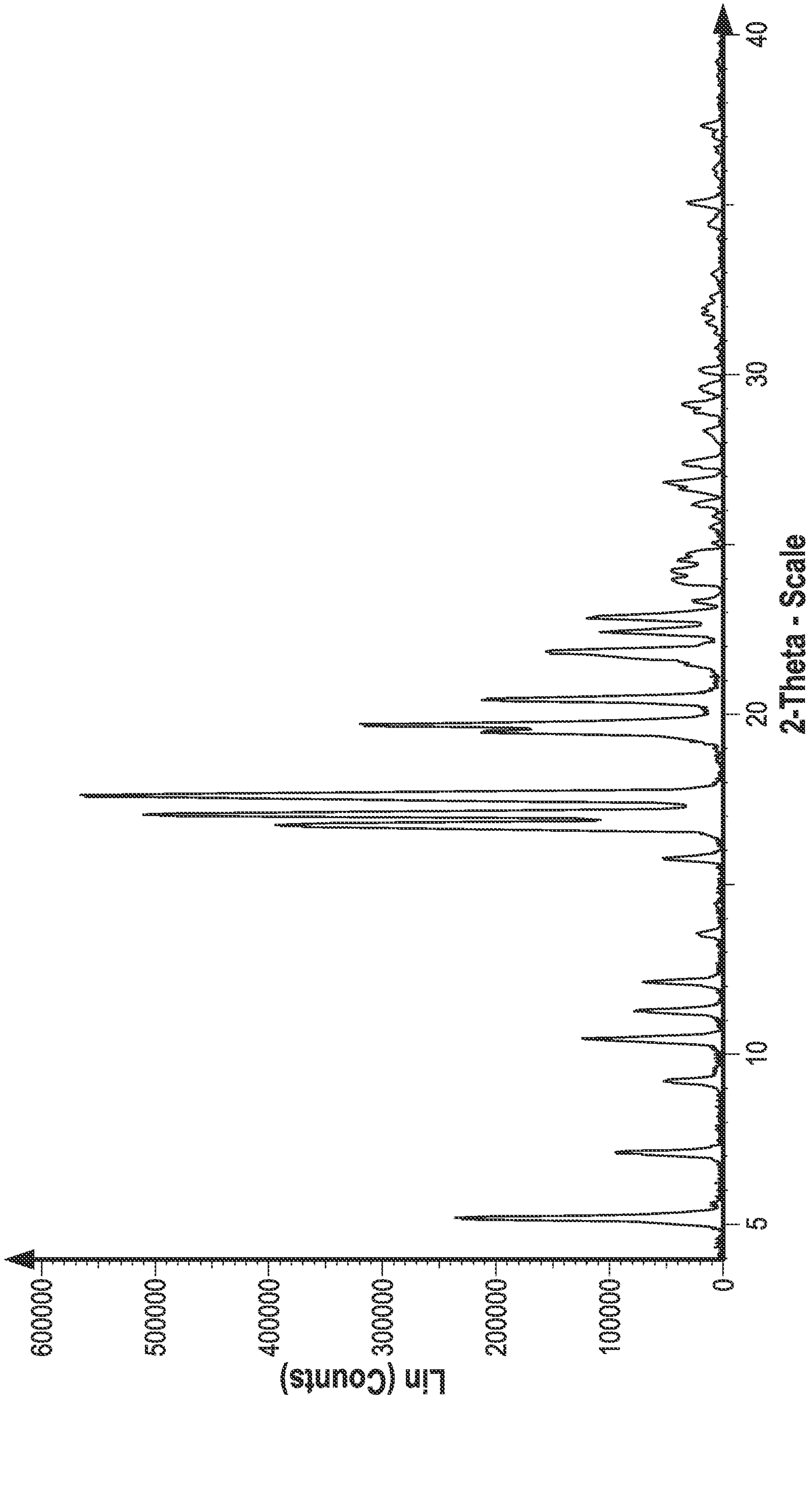
FIG. 1 represents the XRPD patterns of selinexor co-crystal with succinic acid Form I.

The following description is presented to enable a person of ordinary skill in the art to make and use the various embodiments. Descriptions of specific devices, techniques, and applications are provided only as examples. Various modifications to the examples described herein will be clear to those of ordinary skill in the art, and the general principles described herein may be applied to other examples and applications without departing from the spirit and scope of the various embodiments. Therefore, the various embodiments are not intended to be limited to the examples described herein and shown but are to be accorded the scope consistent with the claims.

As used herein and unless otherwise specified, the terms "about" and "approximately," when used in connection with a numeric value or a range of values which is provided to characterize a particular solid form, e.g., a specific temperature or temperature range, such as, e.g., that describing a DSC or TGA thermal event, including, e.g., melting, dehydration, desolvation or glass transition events; a mass change, such as, e.g., a mass change as a function of temperature or humidity; a solvent or water content, in terms of, e.g., mass or a percentage; or a peak position, such as, e.g., in analysis by IR or Raman spectroscopy or XRPD; indicate that the value or range of values may deviate to an extent deemed reasonable to one of ordinary skill in the art while still describing the particular solid form.

As used herein and unless otherwise specified, "co-crystal" and "co-crystal systems" refer to solid materials composed of two or more different coformer molecular compounds in particular stoichiometric ratios which interact through non-covalent interactions which can be designed utilizing supramolecular synthon approach. The co-crystal, in which at least one of the components is selinexor and coformer is a second pharmaceutically acceptable compound, is called a pharmaceutical selinexor co-crystal with the coformer.

As used herein and unless otherwise specified, the term "pharmaceutical composition" is intended to encompass a pharmaceutically effective amount of the selinexor in the co-crystal of the invention and a pharmaceutically acceptable excipient. As used herein, the term "pharmaceutical compositions" includes pharmaceutical compositions such as tablets, pills, powders, liquids, suspensions, emulsions, granules, capsules, suppositories, or injection preparations.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, 23rd ed., 1843-1844 (1995).

As used herein and unless otherwise specified, the term "excipient" refers to a pharmaceutically acceptable organic or inorganic carrier substance. Excipients may be natural or synthetic substances formulated alongside the active ingredient of a medication, included for bulking-up formulations that contain potent active ingredients (thus often referred to as "bulking agents," "fillers," or "diluents"), or to confer a therapeutic enhancement on the active ingredient in the final dosage form, such as facilitating drug absorption or solubility. Excipients can also be useful in the manufacturing process, to aid in the handling of the active substance, such as by facilitating powder flowability or non-stick properties, in addition to aiding in vitro stability such as prevention of denaturation over the expected shelf life.

As used herein and unless otherwise specified, the term "patient" refers to an animal, preferably a mammal, most preferably a human, who has been the object of treatment, observation or experiment. Preferably, the patient has experienced and/or exhibited at least one symptom of the disease or disorder to be treated and/or prevented. Further, a patient may not have exhibited any symptoms of the disorder, disease or condition to be treated and/or prevented, but has been deemed by a physician, clinician or other medical professional to be at risk for developing said disorder, disease or condition.

As used herein and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more therapeutic agents to a patient with such a disease or disorder. In some embodiments, the terms refer to the administration of a compound provided herein, with or without other additional active agents, after the onset of symptoms of a disease.

Particular embodiments of the invention are directed to forms of selinexor co-crystal with succinic acid; more particularly respectively to selinexor co-crystal with succinic acid Forms I and II. Another particular embodiment of the invention is directed to a form of selinexor co-crystal with vanillin; more particularly respectively to selinexor co-crystal with vanillin Form I. Selinexor co-crystal with succinic acid Forms I and II and selinexor co-crystal with vanillin Form I are anhydrous.

The present invention is also related to processes for the preparation of Forms I and II of selinexor co-crystal with succinic acid.

Another embodiment according to the invention for preparing selinexor co-crystal with succinic acid Form I, comprises a) mixing a solution of saturated selinexor and solution of saturated succinic acid in ethyl formate in about $1_{selinexor\ in\ ethyl\ formate}:1_{succinic\ acid\ in\ ethyl\ formate}$ mL ratio to form a mixed solution of selinexor and succinic acid in ethyl formate;
b) adding to the mixed solution of selinexor and succinic acid in ethyl formate solid selinexor and solid succinic acid in a ratio of about 1 $mL_{mixed\ solution\ of\ selinexor\ and\ succinic\ acid\ in\ ethyl\ formate}$:0.25 $mmol_{solid\ selinexor}$:0.375 $mmol_{solid\ succinic\ acid}$;
c) slurrying the mixed solution with the added selinexor and succinic acid; and
d) cooling the solution to yield selinexor co-crystal with succinic acid Form I.

A further embodiment for the proceeding method for preparing the selinexor co-crystal with succinic acid Form I is wherein the slurrying occurs for about 4 hours at about 60° C. Another embodiment is wherein the cooling is undertaken at about −5° C. to 10° C.; more particularly at about 0° C. In yet another embodiment, the method further comprises isolating the selinexor co-crystal with succinic acid Form I by filtration and air drying it for about 2-3 h at about 45° C. A further embodiment is wherein the selinexor co-crystal with succinic acid Form I is 1:1 mol ratio of selinexor: succinic acid.

Yet another embodiment according to the invention is for preparing selinexor co-crystal with succinic acid Form II, comprises a) mixing a solution of selinexor and solution of succinic acid, wherein the solvent of the solution of selinexor or succinic acid is selected from the group consisting of ethyl formate, methanol, 1-propanol, ethyl acetate, isopropanol and acetone, or mixture thereof; to form a mixed solution of selinexor and succinic acid, wherein the ratio of mmol of selinexor:mmol of succinic acid: mL of solvent for selinexor:mL of solvent for succinic acid is about 1 $mmol_{selinexor}$:1-1.5 $mmol_{succinic\ acid}$:3-4 $mL_{solvent\ for\ selinexor}$:3-4 $mL_{solvent\ for\ succinic\ acid}$;

b) adding to the mixed solution of selinexor and succinic acid an anti-solvent, wherein the ratio of mL of mixed solution for selinexor and succinic acid:mL of anti-solvent is about 1 $mL_{mixed\ solution\ for\ selinexor\ and\ succinic\ acid}$:1-3 $mL_{anti\text{-}solvent}$; and c) cooling the mixture of step b) to yield selinexor co-crystal with succinic acid Form II.

A further embodiment for the proceeding method for preparing the selinexor co-crystal with succinic acid Form II is wherein the solvent for dissolving the selinexor or succinic acid is a single solvent or mixture of solvents in about a 3:1 to 9:1 volume ratio. Yet another embodiment is wherein the solvent is 1-propanol, a mixture of 1-propanol and methanol, ethyl acetate and methanol, or ethyl formate and methanol; more particularly a mixture of 1-propanol and methanol, and ethyl acetate and methanol. Still another embodiment is wherein the solution of selinexor is prepared by dissolving the selinexor in a solvent at about 45-60° C.; more particularly at about 50-55° C. Yet another embodiment is wherein the solution of succinic acid is prepared by dissolving the succinic acid in a solvent at about 45-60° C.; more particularly at about 50-55° C. Another embodiment is wherein the anti-solvent is an alkane from $C_5H_{12}$ to $C_8H_{18}$; more particularly $C_7H_{16}$ (heptane). Yet a further embodiment is wherein the addition of the anti-solvent is undertaken at about RT. A further embodiment is wherein the cooling step is carried out at about −5° C. to 10° C.; more particularly at about 0° C. to 5° C. In yet another embodiment, the method further comprises isolating the selinexor co-crystal with succinic acid Form II by filtration and drying it under vacuum for about 8-10 h at about 45° C. A further embodiment is wherein the selinexor co-crystal with succinic acid Form II is 2:3 mol ratio of selinexor:succinic acid.

Another embodiment according to the invention for preparing selinexor co-crystal with vanillin Form I, comprises a) mixing a solution of saturated selinexor and solution of saturated vanillin in tetrahydrofuran in about $1_{selinexor\ in\ tetrahydrofuran}$:$1_{vanillin\ in\ tetrahydrofuran}$ mL ratio to form a mixed solution of selinexor and vanillin in tetrahydrofuran;

b) adding to the mixed solution of selinexor and vanillin in tetrahydrofuran solid selinexor and solid vanillin in a ratio of about 1 $mL_{mixed\ solution\ of\ selinexor\ and\ vanillin\ in\ tetrahydrofuran}$:0.25 $mmol_{solid\ selinexor}$:0.26 $mmol_{solid\ vanillin}$;

c) slurrying the mixed solution with the added selinexor and vanillin; and d) cooling the solution to yield selinexor co-crystal with vanillin Form I.

A further embodiment for the proceeding method for preparing the selinexor co-crystal with vanillin Form I is wherein the slurrying occurs for about 4 hours at about 60° C. Another embodiment is wherein the cooling is undertaken at about −5° C. to 10° C.; more particularly at about 0° C. In yet another embodiment, the method further comprises isolating the selinexor co-crystal with vanillin Form I by filtration and air drying it for about 2-3 h at about 45° C.

Furthermore, the present invention also relates to pharmaceutical compositions comprising selinexor co-crystal with succinic acid Form I or II, or selinexor co-crystal with vanillin Form I, and methods for treating disease using selinexor co-crystal with succinic acid Form I or II, or selinexor co-crystal with vanillin Form I. Pharmaceutical compositions comprising selinexor co-crystal with succinic acid Form I or II, or selinexor co-crystal with vanillin Form I may be prepared according to U.S. Pat. No. 9,714,226, which is incorporated herein by reference in its entirety. XPOVIO® (selinexor) is currently available as 20 mg tablets. The recommended starting dosage of XPOVIO® is 80 mg in combination with dexamethasone taken orally on Days 1 and 3 of each week.

The present disclosure provides for a method of treating a disease comprising administering to a patient, in need thereof, a pharmaceutical composition comprising selinexor co-crystal with succinic acid Form I or II, or selinexor co-crystal with vanillin Form I. XPOVIO® (selinexor) is indicated in combination with dexamethasone for the treatment of adult patients with relapsed or refractory multiple myeloma (RRMM) who have received at least four prior therapies and whose disease is refractory to at least two proteasome inhibitors, at least two immunomodulatory agents, and an anti-CD38 monoclonal antibody.

EXAMPLES

Examples, which follow herein, are directed to embodiments of the invention. The examples are presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Therefore, the various embodiments are illustrative of the present disclosure and the disclosure is not intended to be limited to the examples described herein and shown.

Analytical Techniques

XRPD patterns are obtained using a Bruker D8 Advance equipped with a Cu Kα radiation source (λ=1.54 Å), a 9-position sample holder and a LYNXEYE super speed detector. Samples are placed on air sensitive silicon plate holders with zero-background with domes, for analysis. One skilled in the art would recognize that the °2θ values and the relative intensity values are generated by performing a peak search on the measured data and the d-spacing values are calculated by the instrument from the °2θ values using Bragg's equation. One skilled in the art would further recognize that the relative intensity for the measured peaks may vary because of sample preparation, orientation and instrument used, for example.

DSC data are collected using a TA Instruments Q10 DSC. Approximately, samples (2-8 mg) are placed in unsealed but covered hermetic alodined aluminum sample pans and scanned from about 30 to about 300° C. at a rate of about 10° C./min under a nitrogen purge of about 50 mL/min. Some of the DSC runs are generated on a TA Instruments Q2000 equipped with an auto-sampler and RSC40. The sampling is conducted at a ramp rate of about 10° C./min from 20° C. to 320° C. using Tzero hermetic sealed aluminum sample pans in T4P (or T3) mode.

TGA measurements are recorded using TA Q500 instrument. Approximately, 2-5 mg samples are placed in a pin holed sealed hermetic alodined aluminum DSC pan, pretared with an aluminum pan. TGA investigations are performed at a heating rate of 10.0° C./min over a temperature range of from about 30 to about 300° C., with purging with nitrogen at a flow rate of 60 mL/min.

Sorption isotherms are obtained using a TA Instruments Q5000 SA DVS. The sample temperature is maintained at 25° C. by the instrument controls. The humidity is controlled by mixing streams of dry and wet nitrogen, with a total flow rate of 200 ml/min. The relative humidity is measured by a calibrated probe (dynamic range of 1.0-100% RH), located near the sample. The weight change, (mass relaxation) of the sample as a function of % RH is constantly monitored by a microbalance (accuracy ±0.0001 mg).

Typically, 3-10 mg of sample is placed in a tared mesh stainless steel basket under ambient conditions. The sample is loaded and unloaded at 50% RH and 25° C. (typical room conditions). A moisture sorption isotherm is performed as outlined below (2 scans per complete cycle). The standard isotherm is performed at 25° C. at 10% RH intervals over a 0-90% RH range. Typically, a triple cycle is carried out. Data analysis is carried out using TA Instruments Universal Analysis 2000.

Method for DVS Intrinsic Experiments

| Parameter | Value |
|---|---|
| Desorption-Scan 1 | 50-0 |
| Adsorption Desorption-Scan 2 | 0-90, 90-0 |
| Adsorption Desorption-Scan 3 | 0-90, 90-0 |
| Adsorption Desorption-Scan 4 | 0-90, 90-50 |
| Intervals (% RH) | 10 |
| Number of Scans | 4 |
| Flow Rate (mL/min) | 200 |
| Temperature (° C.) | 25 |
| Stability (° C./min) | 0.1 |
| Sorption Time Per Step (minutes) | minimum 15 minutes, time out at 120 minutes |
| Number of Cycles | 3 |

$^1$H-NMR data is collected using a Bruker Avance 300 MHz NMR equipped with TopSpin software. Samples are prepared by dissolving the compound in deuterated dimethylsulfoxide with 0.05% (v/v) tetramethylsilane (TMS). The number of scans is 16 for $^1$H-NMR.

IR analysis is done by employing solid samples for FTIR using KBr pellet. The pellet is prepared by mixing KBr and the sample in 1:150 ratio (approximately 2-5 mg of the sample with 350 mg of KBr). Omnic software is used for the analysis and the samples are collected with 32 scans.

EXPERIMENTAL

Examples below provide embodiments of the preparation of co-crystal forms of selinexor with succinic acid and a co-crystal form of selinexor with vanillin.

Example 1

Preparation of Selinexor Co-Crystal with Succinic Acid Form I 2 mL of succinic acid saturated ethyl formate is added to 2 mL of selinexor saturated ethyl formate and then 450 mg of selinexor and 180 mg of succinic acid are added to the mixture at room temperature to form a slurry. The slurry is stirred at 60° C. for 4 hours and then cooled overnight (for about 8 h) to 0° C. The thick slurry is vacuum filtered, and then allowed to air dry on a hot plate at 42° C. for several hours (about 2-3 h) to yield selinexor co-crystal with succinic acid Form I.

Figure 2:
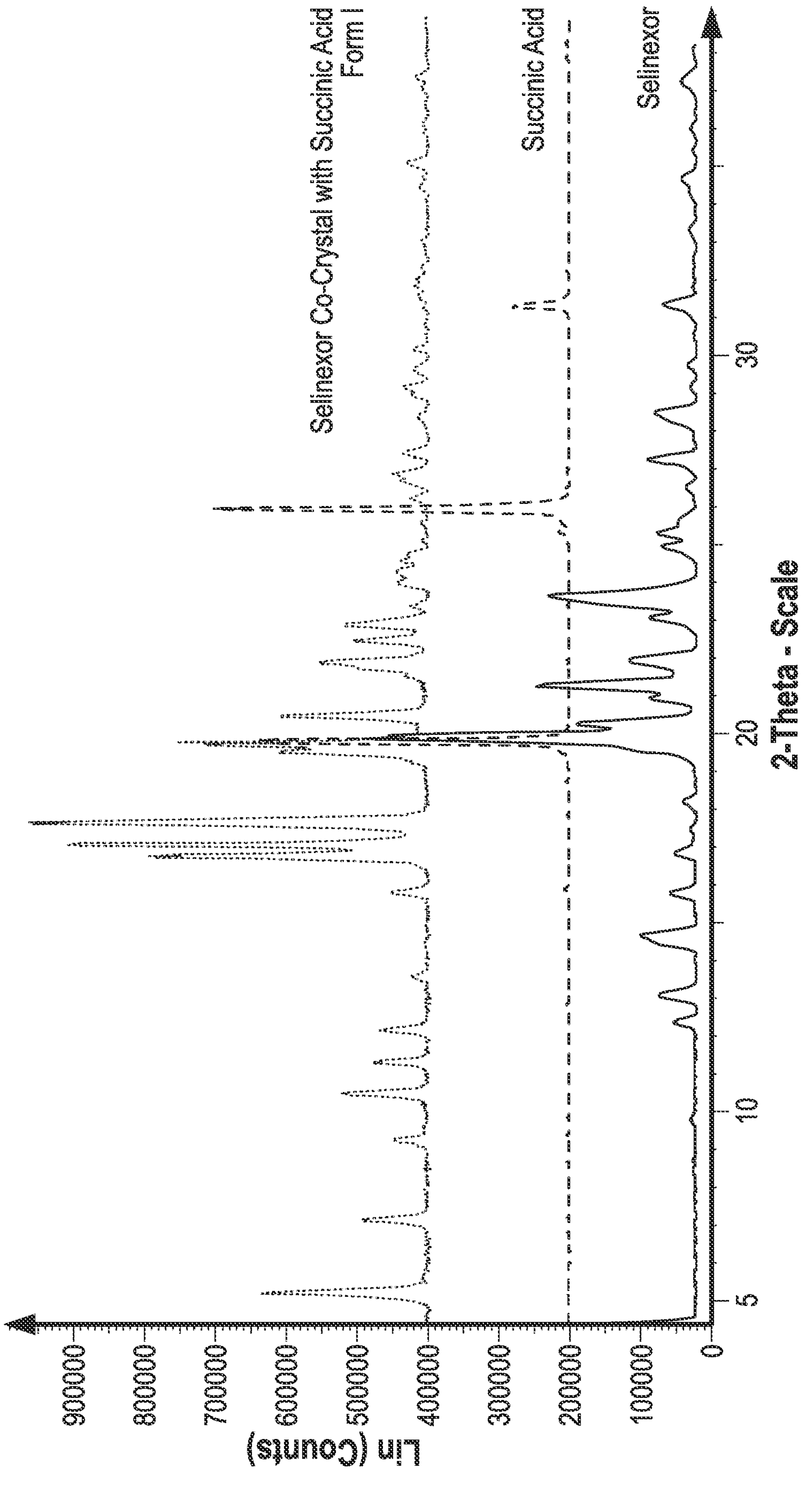
FIG. 2 represents the comparison of the XRPD patterns of selinexor co-crystal with succinic acid Form I, succinic acid and selinexor.

FIG. 1 represents the experimental XRPD pattern of selinexor co-crystal with succinic acid Form I obtained by the instant method. FIG. 2 represents the XRPD pattern of selinexor co-crystal with succinic acid Form I compared to the patterns for co-crystal with succinic acid Form I is characterized by its XRPD pattern peaks and their corresponding intensities that are listed in Table I below.

TABLE I

| Angle 2θ | Intensity % |
|---|---|
| 5.2 | 41.4 |
| 7.1 | 16.3 |
| 9.2 | 8.9 |
| 10.4 | 21.6 |
| 11.3 | 13.4 |
| 12.1 | 12.1 |
| 13.5 | 3.8 |
| 15.8 | 9 |
| 16.7 | 69.5 |
| 17.0 | 90 |
| 17.6 | 100 |
| 19.5 | 38.2 |
| 19.7 | 57.3 |
| 20.4 | 38.5 |
| 21.8 | 28.3 |
| 22.4 | 19.6 |
| 22.9 | 21.4 |
| 23.3 | 4.5 |
| 24.0 | 7.6 |
| 24.2 | 7.9 |
| 24.7 | 5.5 |
| 26.2 | 4.5 |
| 26.8 | 8.8 |
| 27.4 | 6.1 |
| 28.4 | 2.9 |
| 29.1 | 6.3 |
| 29.6 | 3.3 |
| 30.1 | 3.5 |
| 35.1 | 5.4 |
| 37.4 | 3.2 |

The angle measurements are ±0.2° 2θ. Key defining peaks for solid-state selinexor co-crystal with succinic acid Form I include 5.2, 16.7, 17.0, 17.6 and 19.7° 2θ.

Figure 3:
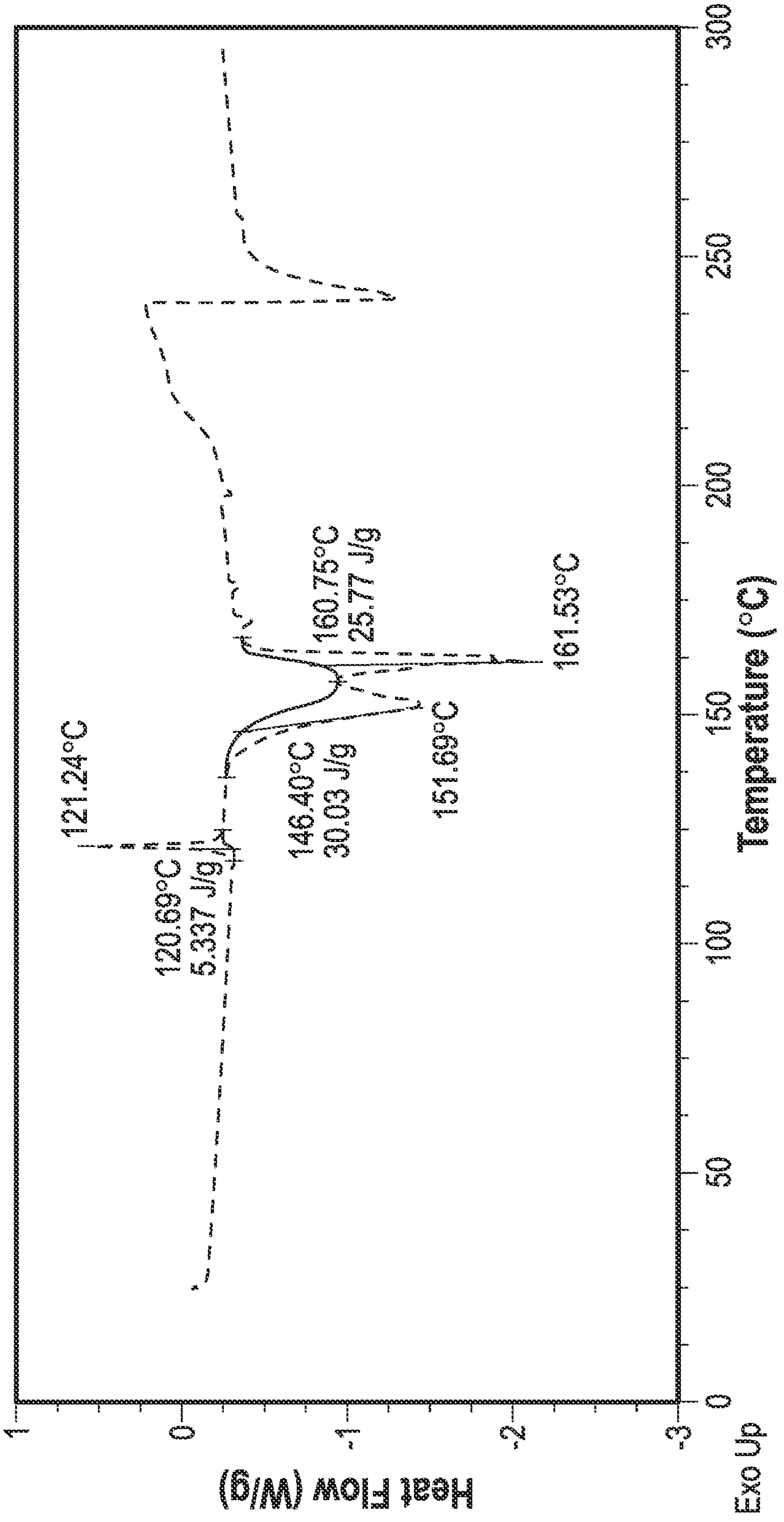
FIG. 3 is a DSC plot of selinexor co-crystal with succinic acid Form I.
Figure 4:
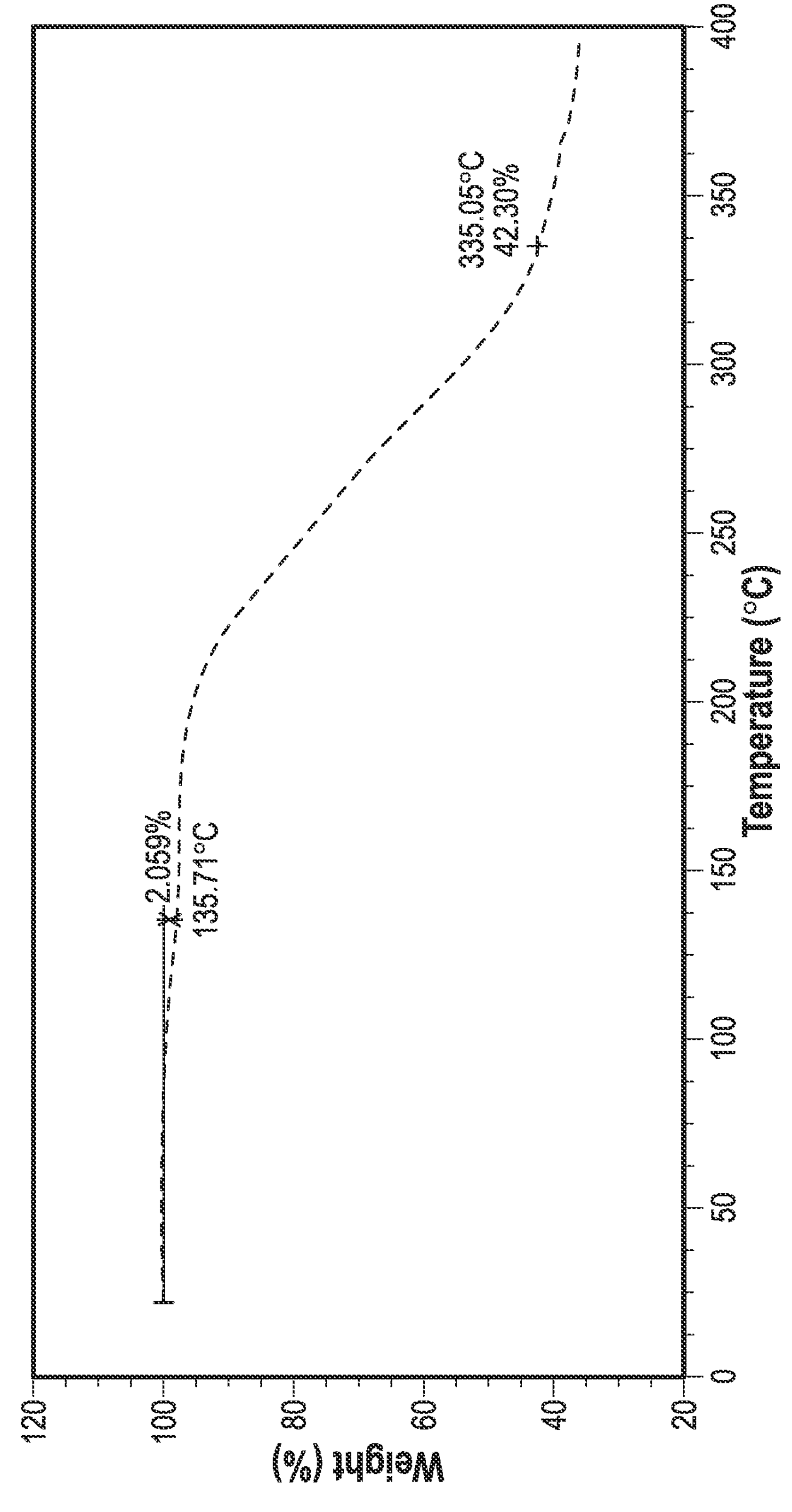
FIG. 4 is a TGA plot of selinexor co-crystal with succinic acid Form I.
Figure 5:
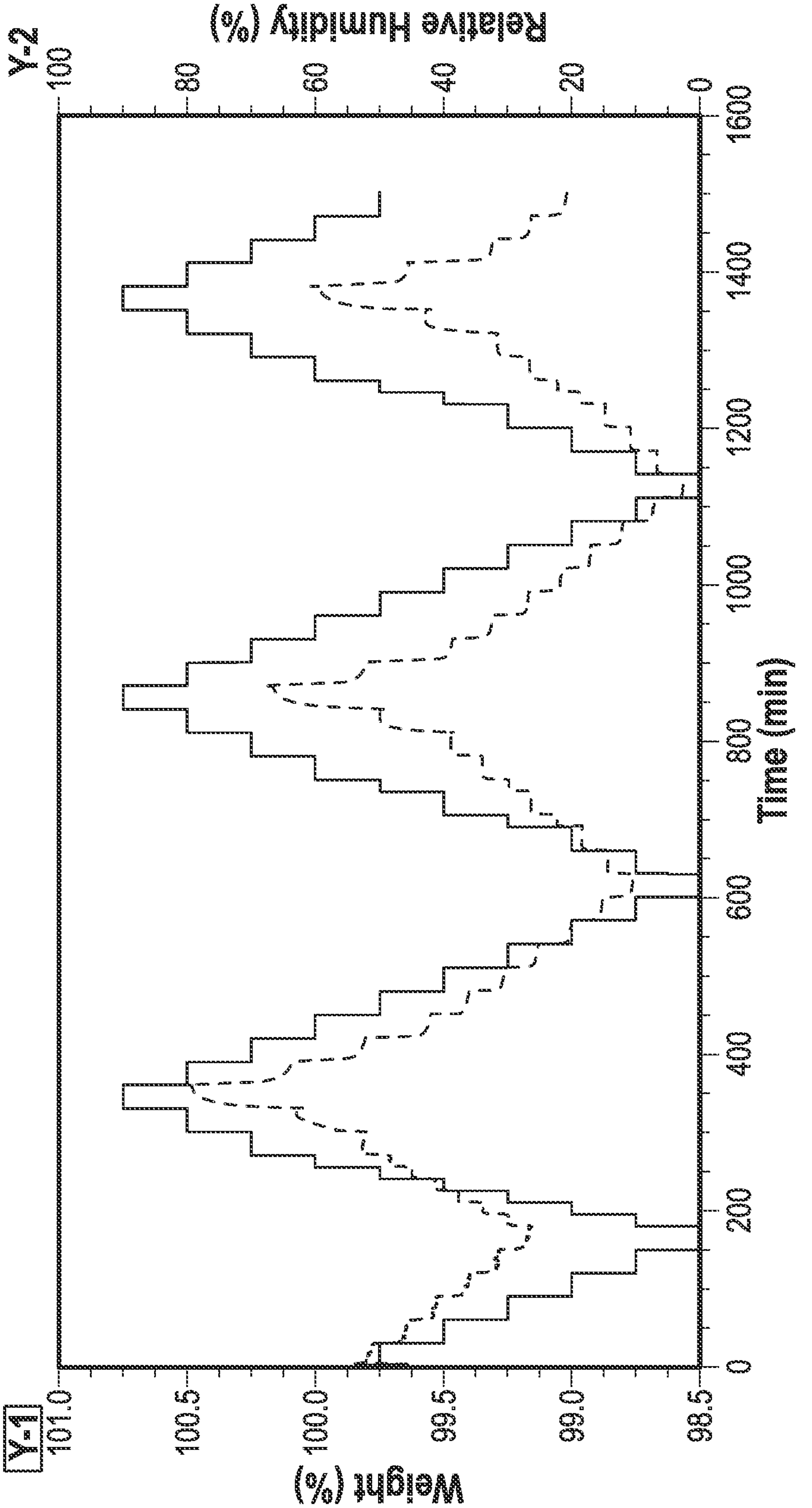
FIG. 5 is a DVS plot of selinexor co-crystal with succinic acid Form I.
Figure 6:
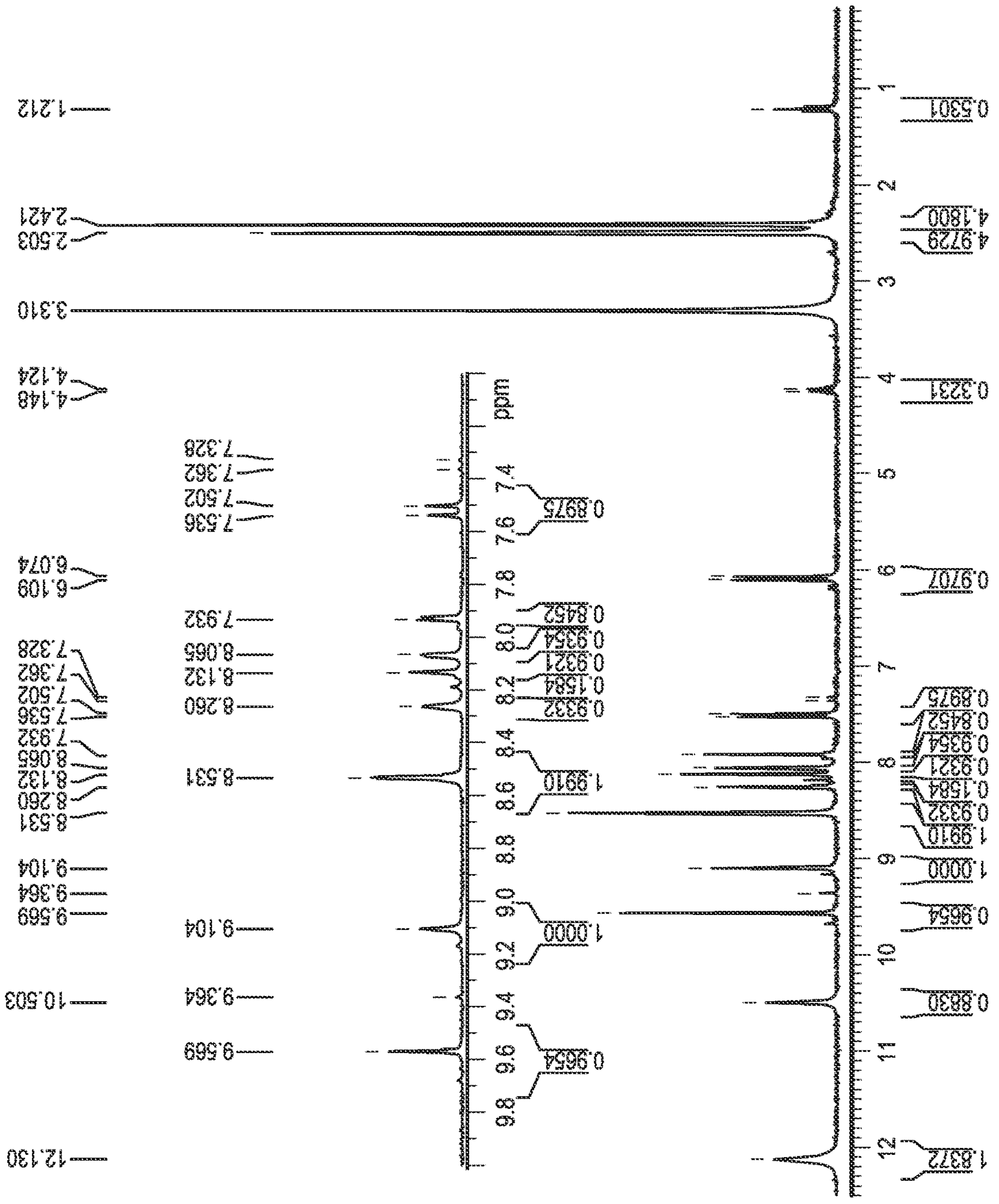
FIG. 6 is a $^1$H NMR spectra of selinexor co-crystal with succinic acid Form I.
Figure 7:
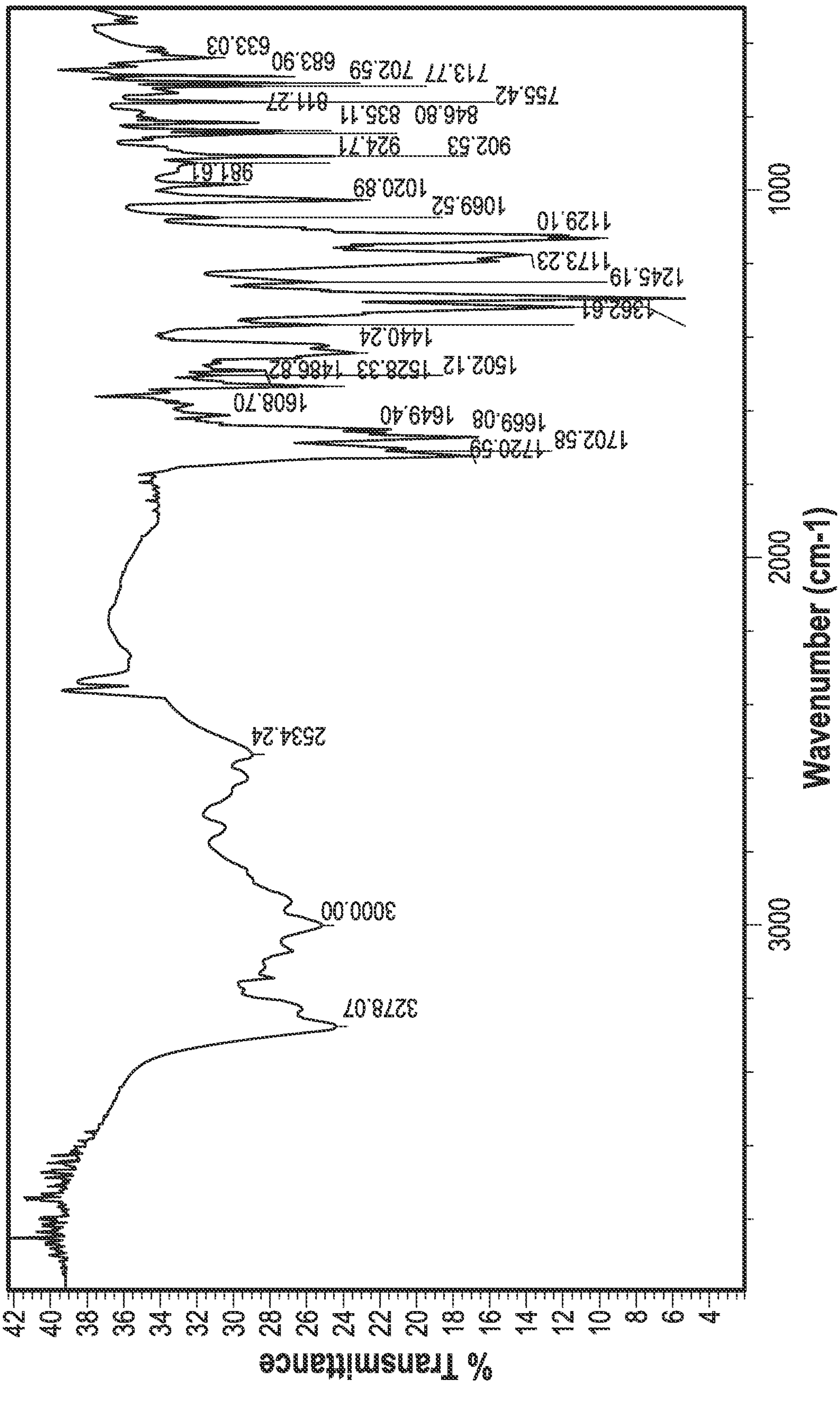
FIG. 7 is directed to FT-IR spectra of selinexor co-crystal with succinic acid Form I.
Figure 8:
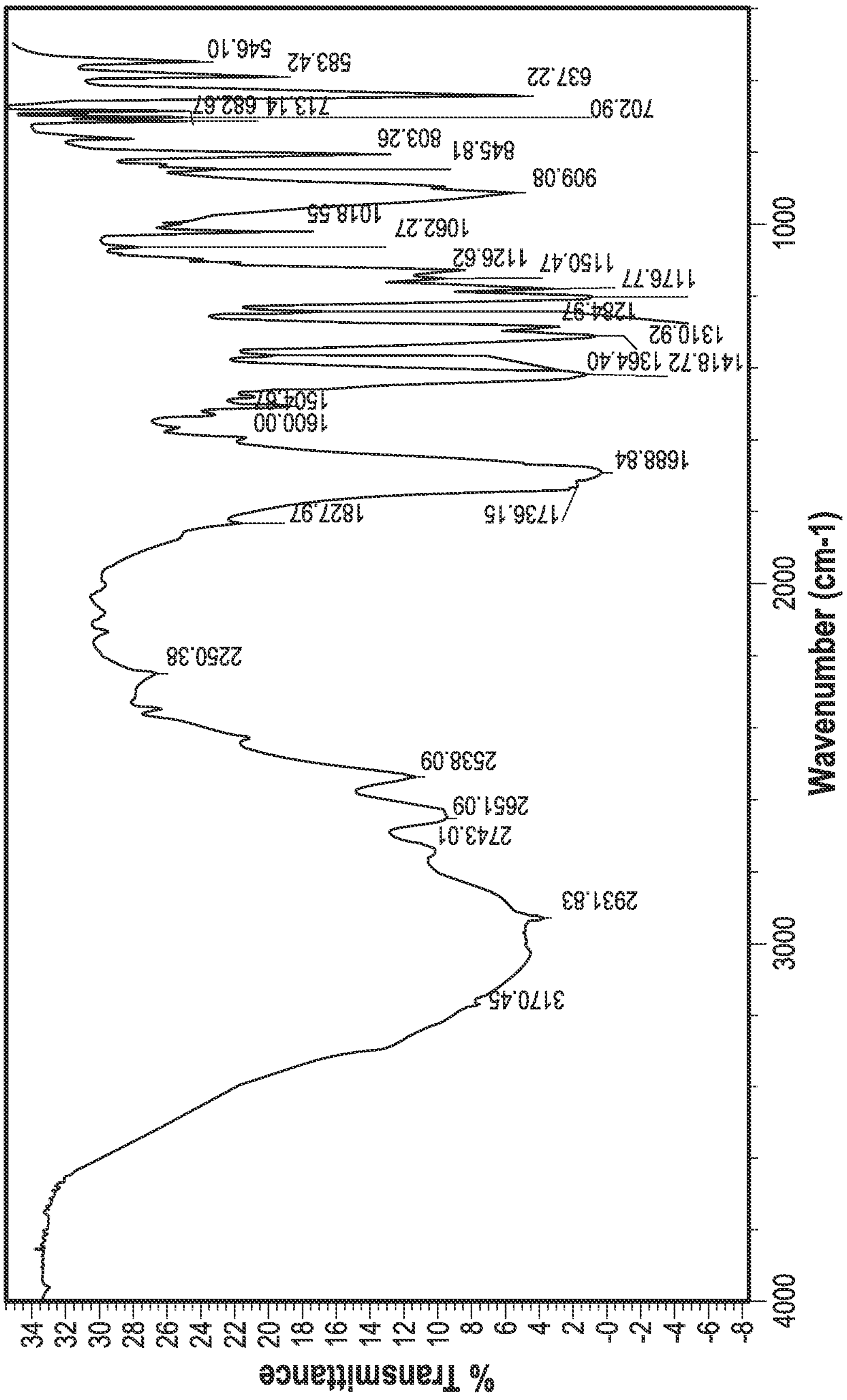
FIG. 8 is directed to FT-IR spectra a physical non-binding mixture of selinexor and succinic acid.

The DSC plot (FIG. 3) shows three thermal events at about 121° C., 152° C. and 162° C. for selinexor co-crystal with succinic acid Form I. The TGA plot (FIG. 4) shows TGA weight loss of about 2.0% from about 100° C. through about 135° C. for selinexor co-crystal with succinic acid Form I. FIG. 5 shows the DVS for selinexor co-crystal with succinic acid Form I and that it is susceptible to adsorbing water. Such adsorption does help with the solubility of the co-crystal as opposed to selinexor that does not adsorb water and has low solubility. FIG. 6 is an $^1$H NMR spectra for the selinexor co-crystal with succinic acid Form I. FIG. 7 is directed to FT-IR spectra of selinexor co-crystal with succinic acid Form I versus FIG. 8 that is directed to FT-IR spectra of non-binding physical mixture of selinexor and succinic acid.

Example 2

Preparation of Selinexor Co-Crystal with Succinic Acid Form II

Method 1

Selinexor (2.59 g, 5.85 mmols) is dissolved in 18 mL ethyl formate and 2 mL acetone at 55° C. Succinic acid (0.69 g, 5.84 mmols) is dissolved in 15 mL ethyl formate and 5 mL of MeOH at 55° C., or 20 mL of 1-propanol. The selinexor and succinic acid solutions are mixed together in a flask and then 100 mL of heptane is added at room temperature. The resultant mixture is cooled to 5° C. and stirred overnight to yield a precipitant. The precipitant is isolated by filtering and then dried at 45° C. in an oven overnight (8-10 h) to yield selinexor co-crystal with succinic acid Form II.

Method 2

Selinexor (2.59 g, 5.85 mmols) is dissolved in 14 mL methanol and 4 mL 1-propanol at 50° C. Succinic acid (0.69 g, 5.84 mmols) is dissolved in 14 mL 1-propanol and 4 mL of MeOH at 50° C. The selinexor and succinic acid solutions are mixed together at 50° C. in a flask and then 120 mL of heptane is added. The resultant mixture is cooled to 5° C. and stirred 2-3 h to yield a precipitant. The precipitant is isolated by filtering and then dried at 45° C. in an oven overnight (8-10 h) to yield selinexor co-crystal with succinic acid Form II.

Figure 9:
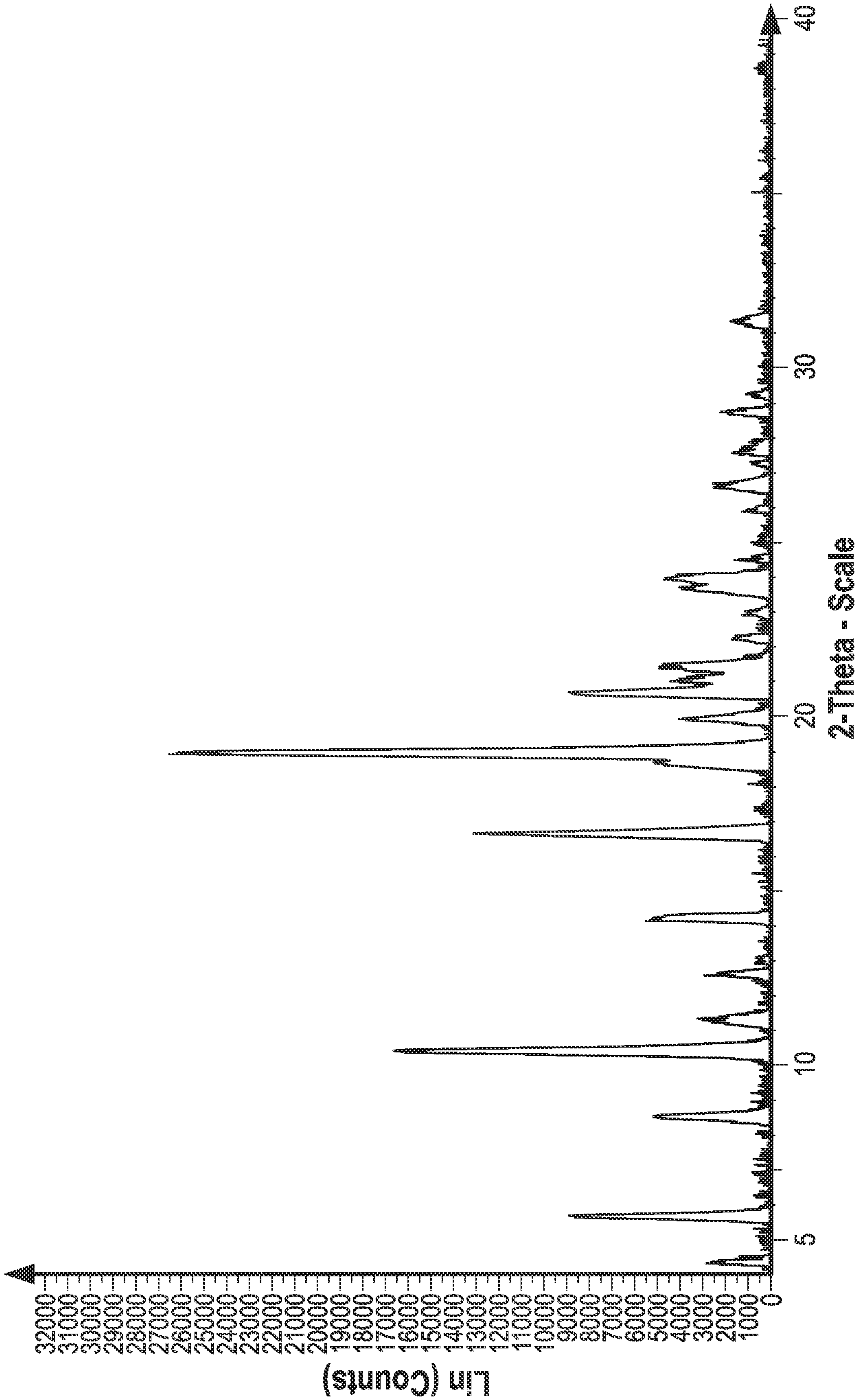
FIG. 9 represents the XRPD patterns of selinexor co-crystal with succinic acid Form II.
Figure 10:
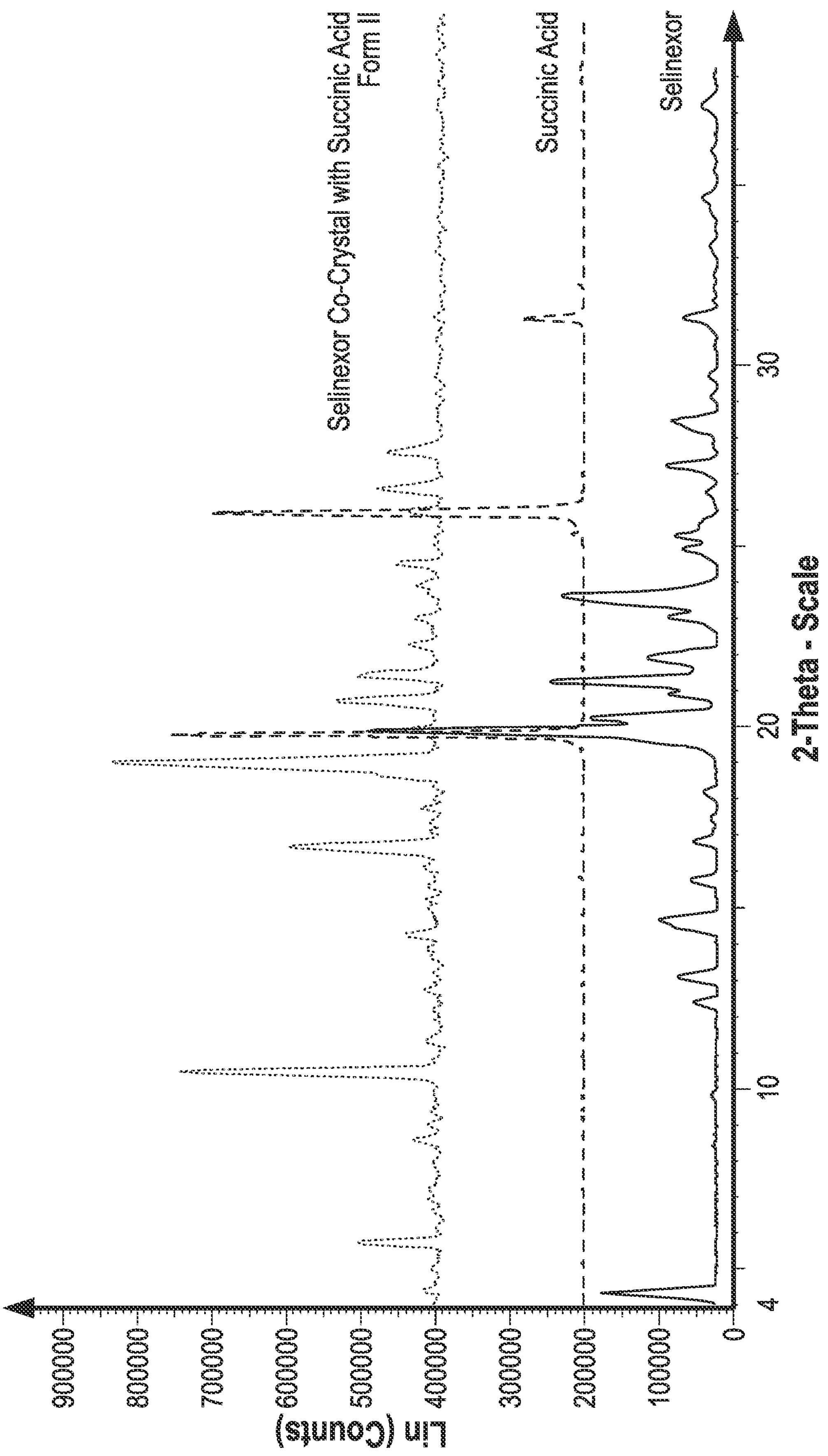
FIG. 10 represents the comparison of the XRPD patterns of selinexor co-crystal with succinic acid Form II, succinic acid and selinexor.

FIG. 9 represents the experimental XRPD pattern of selinexor co-crystal with succinic acid Form II obtained by the instant method. FIG. 10 represents the XRPD pattern of selinexor co-crystal with succinic acid Form II compared to the patterns for selinexor and succinic acid. Selinexor co-crystal with succinic acid Form II is characterized by its XRPD pattern peaks and their corresponding intensities that are listed in Table II below.

TABLE II

| Angle 2θ | Intensity % |
|---|---|
| 5.7 | 27.1 |
| 8.6 | 10.8 |
| 10.4 | 80.2 |
| 14.2 | 14.3 |
| 16.6 | 48.9 |
| 18.9 | 100 |
| 19.9 | 14.8 |
| 20.7 | 34.9 |
| 21.4 | 28.7 |
| 22.2 | 12.6 |
| 23.0 | 11.2 |
| 23.8 | 8.4 |
| 24.5 | 16.6 |
| 25.9 | 12.3 |
| 26.6 | 21.8 |
| 27.6 | 19.8 |

The angle measurements are ±0.2° 2θ. Key defining peaks for solid-state selinexor co-crystal with succinic acid Form II include 10.4, 16.6, 18.9 and 20.7° 2θ.

Figure 11:
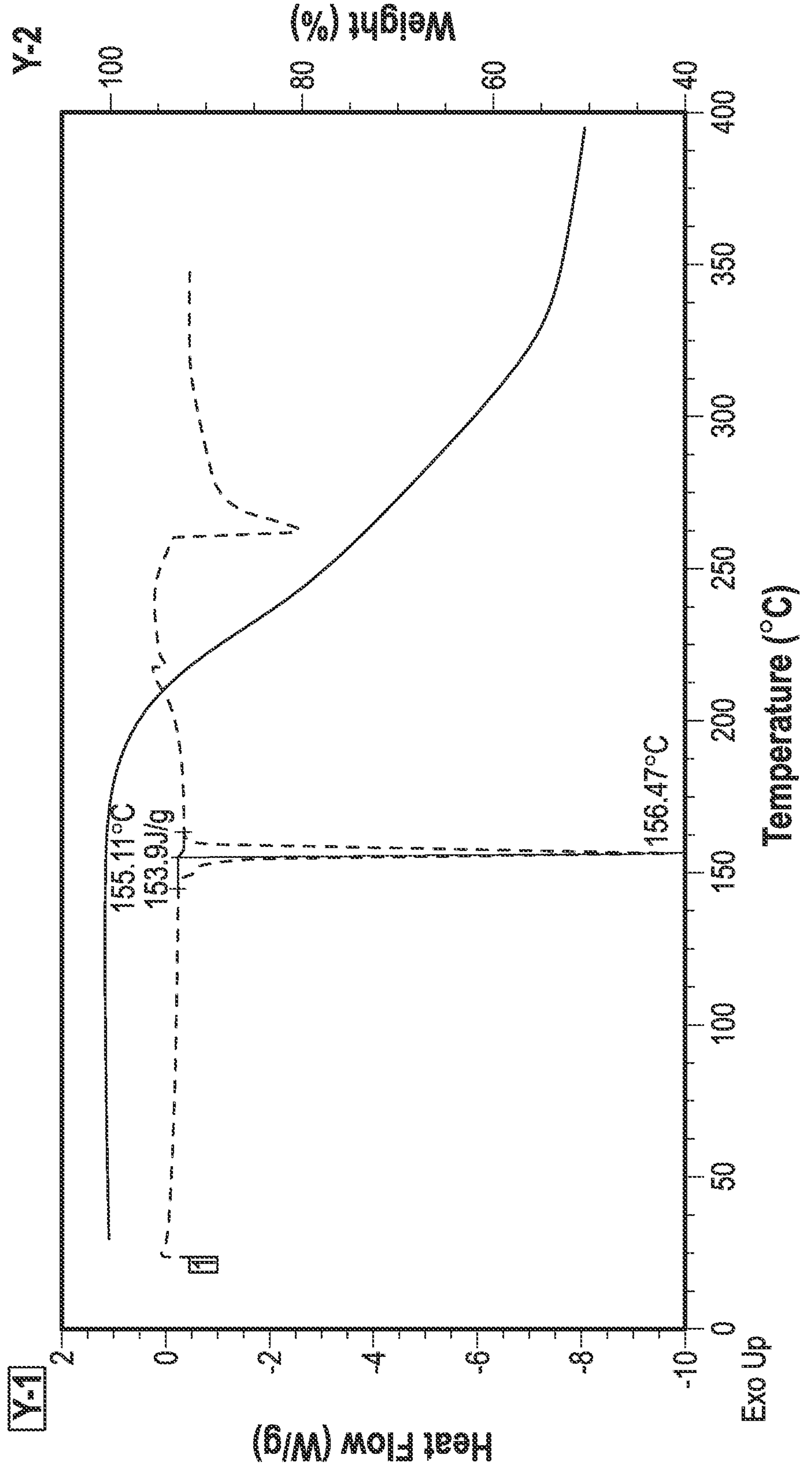
FIG. 11 shows the DSC and TGA plots of selinexor co-crystal with succinic acid Form II.
Figure 12:
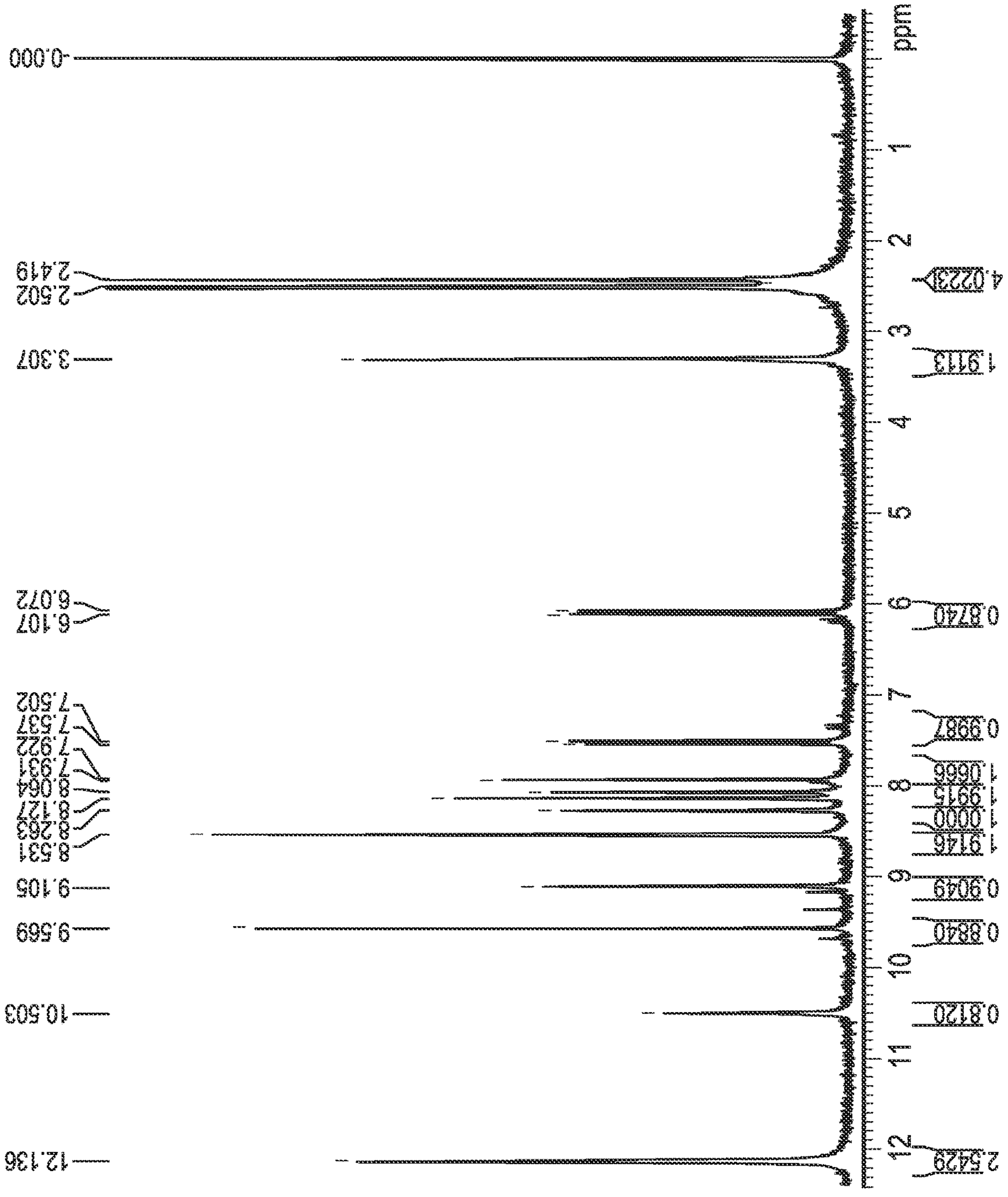
FIG. 12 is a $^1$H NMR spectra of selinexor co-crystal with succinic acid Form II.
Figure 13:
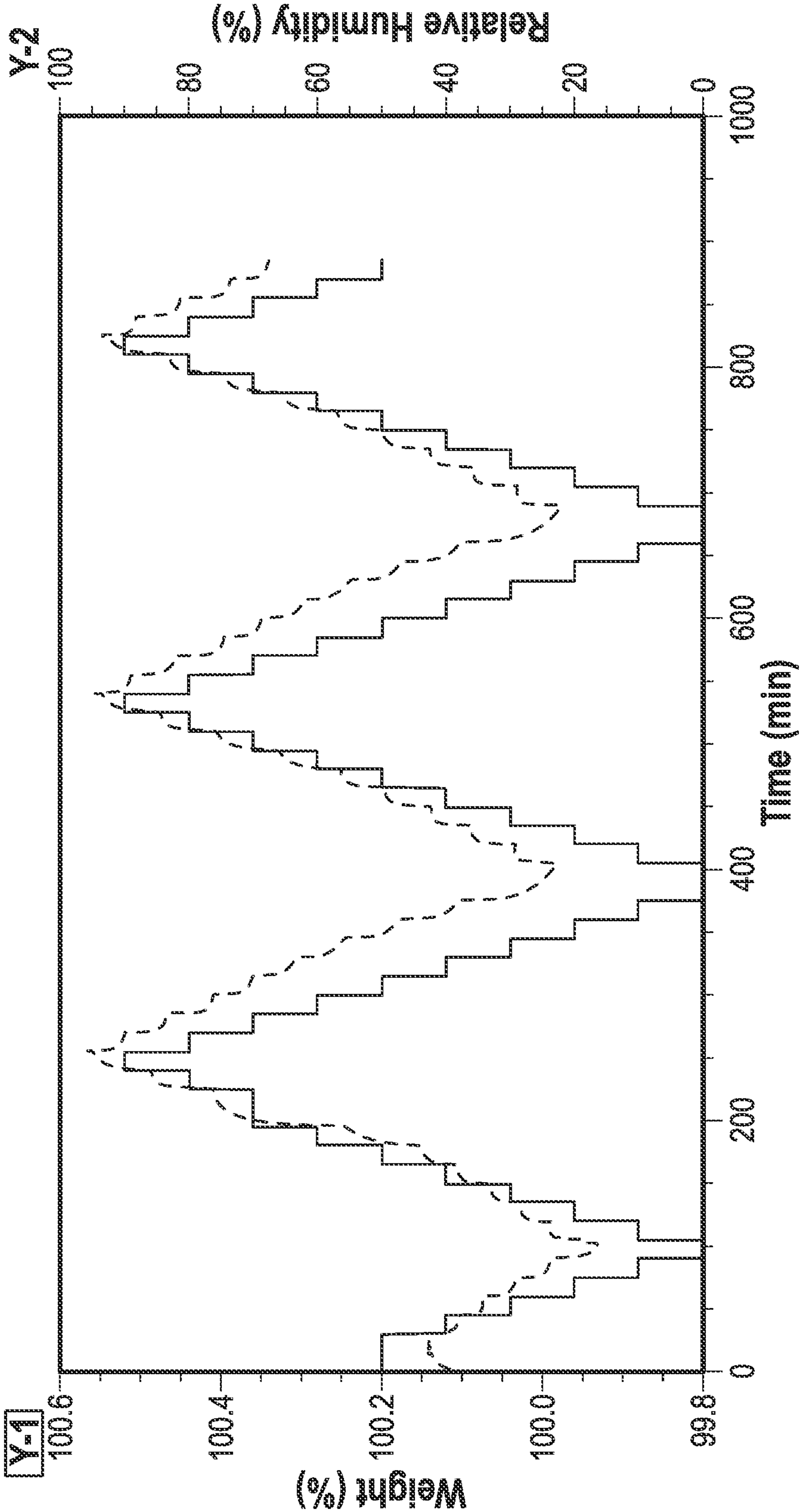
FIG. 13 is a DVS plot of selinexor co-crystal with succinic acid Form II.
Figure 14:
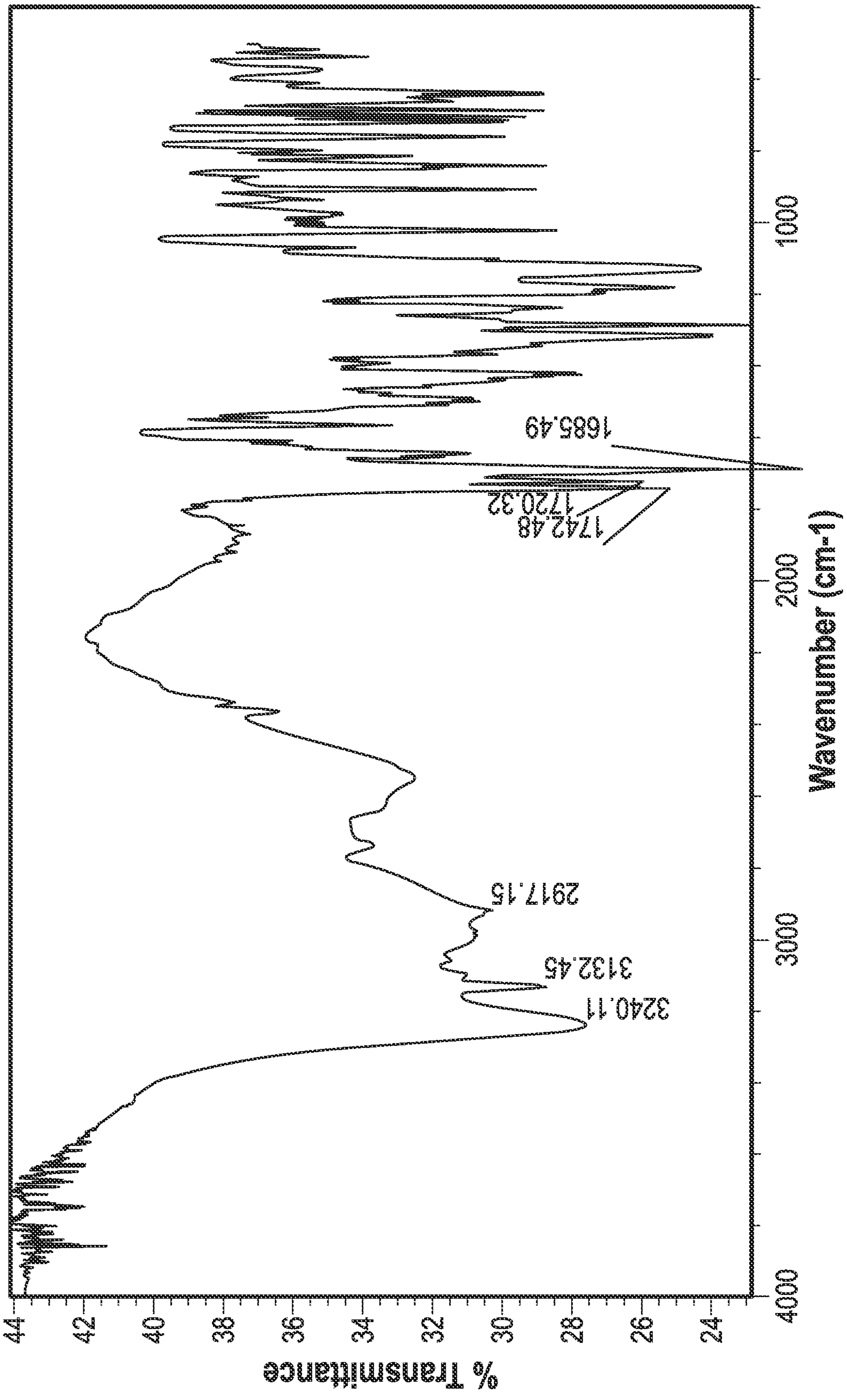
FIG. 14 is directed to FT-IR spectra of selinexor co-crystal with succinic acid Form II.

FIG. 11 shows both the DSC and TGA plots. The DSC plot shows one thermal event at about 156° C. for selinexor co-crystal with succinic acid Form II. FIG. 12 is an $^{1}$H NMR spectra for the selinexor co-crystal with succinic acid Form II. FIG. 13 shows the DVS for selinexor co-crystal with succinic acid Form II and that it is susceptible to adsorbing water. Such adsorption does help with the solubility of the co-crystal as opposed to selinexor that does not adsorb water and has low solubility. FIG. 14 is directed to FT-IR spectra of selinexor co-crystal with succinic acid Form II.

Example 3

Preparation of Selinexor Co-Crystal with Vanillin Form I 2 mL of vanillin saturated tetrahydrofuran is added to 2 mL of selinexor saturated tetrahydrofuran and then 450 mg of selinexor and 160 mg of vanillin are added to the mixture at room temperature to form a slurry. The slurry is stirred at 60° C. for 4 hours and then cooled overnight (for about 8 h) to 0° C. The thick slurry is vacuum filtered, and then allowed to air dry on a hot plate at 42° C. for several hours (about 2-3 h) to yield selinexor co-crystal with vanillin Form I.

Figure 15:
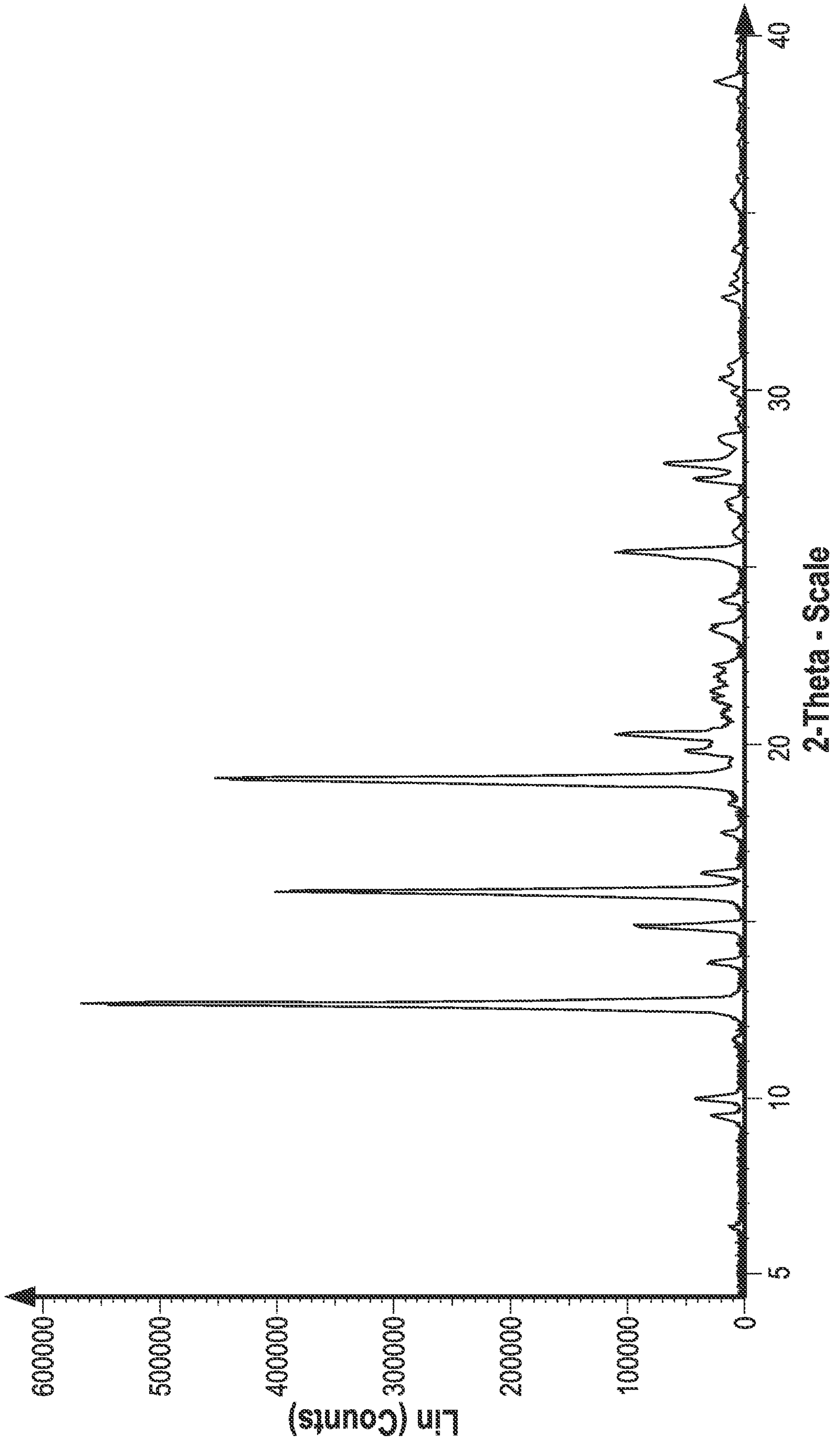
FIG. 15 represents the XRPD patterns of selinexor co-crystal with vanillin Form I.
Figure 16:
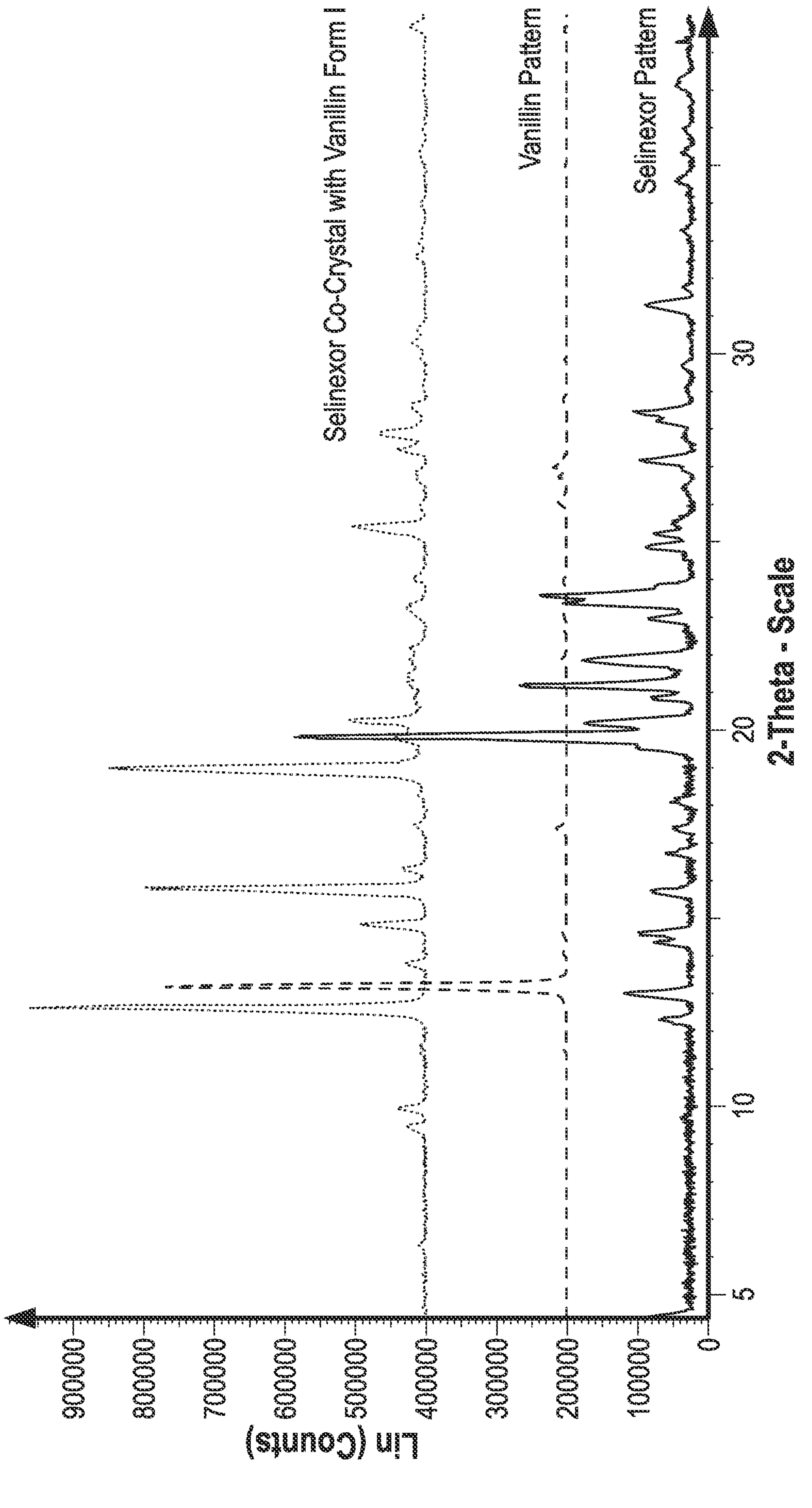
FIG. 16 represents the comparison of the XRPD patterns of selinexor co-crystal with vanillin Form I, vanillin and selinexor.

FIG. 15 represents the experimental XRPD pattern of selinexor co-crystal with vanillin Form I obtained by the instant method. FIG. 16 represents the XRPD pattern of selinexor co-crystal with vanillin Form I compared to the patterns for selinexor and vanillin. Selinexor co-crystal with vanillin Form I is characterized by its XRPD pattern peaks and their corresponding intensities that are listed in Table III below.

TABLE III

| Angle | Intensity % |
|---|---|
| 6.3 | 1.8 |
| 9.4 | 4.3 |
| 9.9 | 6.7 |
| 12.6 | 100 |
| 13.7 | 5 |
| 14.8 | 16.2 |
| 15.8 | 70.5 |
| 16.3 | 5.6 |
| 17.4 | 2.9 |
| 19.0 | 78.3 |
| 19.8 | 6.4 |
| 20.2 | 17.1 |
| 22.2 | 3.1 |
| 23.2 | 4.6 |
| 24.0 | 3.1 |
| 25.4 | 18.6 |
| 25.9 | 1.1 |
| 26.8 | 2 |
| 27.4 | 6.9 |
| 27.9 | 11.2 |
| 28.6 | 3.1 |
| 30.3 | 2.9 |
| 32.6 | 2.3 |
| 35.3 | 1.4 |
| 38.7 | 3.9 |

The angle measurements are ±0.2° 2θ. Key defining peaks for solid-state selinexor co-crystal with vanillin Form I include 12.6, 15.8, and 19.0° 2θ.

The above examples are presented to aid in the understanding of the disclosure and enable a person of ordinary skill in the art to make and use the various embodiments, and are not intended and should not be construed to limit in any way the disclosure set forth in the claims which follow hereafter.

What is claimed is:

1. A selinexor co-crystal comprising selinexor and succinic acid as a coformer.

2. The selinexor co-crystal of claim 1, wherein the selinexor co-crystal is crystalline Form I characterized by X-ray powder diffraction peaks at 2θ angles of about 5.2°, 16.7°, 17.0°, 17.6°, and 19.7°.

3. The selinexor co-crystal of claim 2, having one to three thermal events with onsets selected from about 121° C., 146° C. and 161° C., as measured by differential scanning calorimetry.

4. The selinexor co-crystal of claim 1, characterized by having one or more X-ray powder diffraction peaks selected from 2θ angles of about 5.2°, 16.7°, 17.0°, 17.6° and 19.7°.

5. The selinexor co-crystal of claim 1, characterized by having two or more X-ray powder diffraction peaks selected from 2θ angles of about 5.2°, 16.7°, 17.0°, 17.6° and 19.7°.

6. The selinexor co-crystal of claim 1, wherein the selinexor co-crystal is crystalline Form II characterized by X-ray powder diffraction peaks at 2θ angles of about 10.4°, 16.6°, 18.9°, and 20.7°.

7. The selinexor co-crystal of claim 6, having a thermal event with an onset at about 155° C., as measured by differential scanning calorimetry.

8. The selinexor co-crystal of claim 1, characterized by having one or more X-ray powder diffraction peaks selected from 20 angles of about 10.4°, 16.6°, 18.9°, and 20.7°.

9. The selinexor co-crystal of claim 1, characterized by having one or more X-ray powder diffraction peaks selected from 2θ angles of about 10.4°, 16.6°, 18.9°, and 20.7°.

10. A selinexor co-crystal comprising selinexor with vanillin as a coformer.

11. The selinexor co-crystal of claim 10, wherein the selinexor co-crystal is crystalline Form I characterized by having X-ray powder diffraction peaks at 2θ angles of about 12.6°, 15.8°, and 19.0°.

12. The selinexor co-crystal of claim 11, characterized by having X-ray powder diffraction peaks at 2θ angles of about 12.6°, 14.8°, 15.8°, 19.0°, 20.2°, 25.4°, and 27.9°.

13. A process for the preparation of selinexor co-crystal of claim 2, comprising a) mixing a solution of saturated selinexor and solution of saturated succinic acid in ethyl formate in about 1 (selinexor in ethyl formate): 1 (succinic acid in ethyl formate) mL ratio to form a mixed solution of selinexor and succinic acid in ethyl formate;

b) adding to the mixed solution of selinexor and succinic acid in ethyl formate solid selinexor and solid succinic acid in a ratio of about 1 mL (mixed solution of selinexor and succinic acid in ethyl formate): 0.25 mmol (solid selinexor): 0.375 mmol (solid succinic acid) solid succinic acid;

c) slurrying the mixed solution with the added selinexor and succinic acid; and d) cooling the solution to yield the selinexor co-crystal.

14. A process for the preparation of selinexor co-crystal of claim 6, comprising a) mixing a solution of selinexor and solution of succinic acid, wherein the solvent of the solution of selinexor or succinic acid is selected from the group consisting of ethyl formate, methanol, 1-propanol, ethyl acetate, isopropanol and acetone, or mixture thereof; to form a mixed solution of selinexor and succinic acid, wherein the ratio of mmol of selinexor:mmol of succinic acid: mL of solvent for selinexor:mL of solvent for succinic acid is about 1 mmol (selinexor): 1-1.5 mmol (succinic acid): 3-4 mL (solvent for selinexor): 3-4 mL (solvent for succinic acid) solvent for succinic acid, b) adding to the mixed solution of selinexor and succinic acid an anti-solvent, wherein the ratio of mL of mixed solution for selinexor and succinic acid:mL of anti-solvent is about 1 mL (mixed solution for selinexor and succinic acid): 2-4 mL (anti-solvent) anti-solvent; and c) cooling the mixture of step b) to yield the selinexor co-crystal.

15. A process for preparing selinexor co-crystal of claim 10, comprising a) mixing a solution of dissolved selinexor and solution of dissolved vanillin in tetrahydrofuran in about 1 (selinexor in tetrahydrofuran): 1 (vanillin in tetrahydrofuran) mL ratio to form a mixed solution of selinexor and vanillin in tetrahydrofuran;

b) adding to the mixed solution of selinexor and vanillin in tetrahydrofuran solid selinexor and solid vanillin in a ratio of about 1 mL (mixed solution of selinexor and vanillin in tetrahydrofuran) mixed solution of selinexor and vanillin in tetrahydrofuran: 0.25 mmol (solid selinexor) solid selinexor: 0.26 mmol (solid vanillin) solid vanillin;

c) slurrying the mixed solution with the added selinexor and vanillin; and d) cooling the solution to yield the selinexor co-crystal.

16. The selinexor co-crystal of claim 2, characterized by having X-ray powder diffraction peaks at 2θ angles of about 5.2°, 10.4°, 16.7°, 17.0°, 17.6°, 19.5°, 19.7°, 20.4°, 21.8°, and 22.9°.

17. The selinexor co-crystal of claim 2, characterized by having X-ray powder diffraction peaks at 2θ angles of about 5.2°, 7.1°, 10.4°, 11.3°, 12.1°, 16.7°, 17.0°, 17.6°, 19.5°, 19.7°, 20.4°, 21.8°, and 22.9°.

18. The selinexor co-crystal of claim 6, characterized by having X-ray powder diffraction peaks at 2θ angles of about 5.7°, 10.4°, 14.2°, 16.6°, 18.9°, 20.7°, 21.4°, 22.2°, 23.0°, 24.5°, 25.9°, 26.6°, and 27.6°.

19. The selinexor co-crystal of claim 6, characterized by having X-ray powder diffraction peaks at 2θ angles of about 5.7°, 10.4°, 16.6°, 18.9°, 20.7°, 21.4°, 24.5°, 26.6°, and 27.6°.

* * * * *